(12) United States Patent
Desouhant-Massacret

(10) Patent No.: US 9,403,745 B2
(45) Date of Patent: *Aug. 2, 2016

(54) METHOD FOR SEPARATING SALIFIED PHENOLIC COMPOUNDS

(71) Applicant: RHODIA OPERATIONS, Paris (FR)

(72) Inventor: Magali Desouhant-Massacret, Caluire (FR)

(73) Assignee: Rhodia Operations, Aubervilliers (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/737,554

(22) Filed: Jun. 12, 2015

(65) Prior Publication Data

US 2015/0274625 A1 Oct. 1, 2015

Related U.S. Application Data

(63) Continuation of application No. 13/499,833, filed as application No. PCT/EP2010/064602 on Sep. 30, 2010, now Pat. No. 9,079,842.

(30) Foreign Application Priority Data

Oct. 2, 2009 (FR) ..................... 09 04701

(51) Int. Cl.
*C07C 39/10* (2006.01)
*C07C 41/36* (2006.01)
*C07C 45/67* (2006.01)
*C07C 51/47* (2006.01)

(52) U.S. Cl.
CPC ................. *C07C 41/36* (2013.01); *C07C 45/67* (2013.01); *C07C 51/47* (2013.01)

(58) Field of Classification Search
USPC ......................... 568/432, 758, 763
See application file for complete search history.

(56) References Cited

U.S. PATENT DOCUMENTS

| 4,186,085 A | 1/1980 | Savage |
| 5,094,754 A | 3/1992 | Maroldo et al. |
| 5,124,490 A * | 6/1992 | Cipullo ................. C07C 37/82 568/724 |
| 6,359,172 B1 | 3/2002 | Kessels |
| 6,753,441 B1 | 6/2004 | Jouve et al. |
| 9,079,842 B2 * | 7/2015 | Desouhant-Massacret ............ C07C 41/36 |
| 2011/0230674 A1 | 9/2011 | Desouhant-Massacret |

FOREIGN PATENT DOCUMENTS

FR 2931476 A1 11/2009
WO WO 9965853 A1 12/1999

OTHER PUBLICATIONS

Meier et al.—Atlas of Zeolite Structure Types published by the Structure Commission of the International Zeolite Association (308 pages), 2001.

* cited by examiner

*Primary Examiner* — Pancham Bakshi
(74) *Attorney, Agent, or Firm* — Osha Liang LLP

(57) ABSTRACT

A method for separating a salified phenolic compound from a reaction medium including same is described. Also described, is a method for separating salified phenolic compounds from an aqueous reaction medium resulting from the reaction of a phenolic compound and glyoxylic acid in the presence of a base, which leads to a reaction medium including at least the excess of the starting salified phenolic compound and the various salified mandelic compounds resulting from the reaction, wherein the reaction medium including the starting salified phenolic compound is contacted with an adsorbent substrate. This leads to the selective adsorption of the phenolic compound onto said substrate and to the recovery of an aqueous flow containing the salified mandelic compounds from the reaction, and in that the phenolic compound attached onto the adsorbent is desorbed by means of a regenerating treatment of the adsorbent.

23 Claims, No Drawings

METHOD FOR SEPARATING SALIFIED PHENOLIC COMPOUNDS

CROSS-REFERENCE TO RELATED APPLICATIONS

The present application is a continuation application of U.S. patent application Ser. No. 13/499,833 filed Apr. 2, 2012, which is a U.S. national stage entry under 35 U.S.C. §371 of International Application No. PCT/EP2010/064602 filed Sep. 30, 2010 and designating the United States (published on Apr. 7, 2011, as WO 2011/039331 A1; the title and abstract were also published in English), which claims priority to French application no. 09 04701, filed on Oct. 2, 2009, the whole content of these applications being herein incorporated by reference for all purposes.

TECHNICAL FIELD OF THE INVENTION

The present invention provides a method of separating phenolic compounds in salified form from a reaction mixture comprising them.

More specifically, the invention relates to the separation of guaiacol or of guaethol in salified form from the synthesis mixtures comprising them.

The invention is directed more particularly to the recovery of guaiacol in the form of sodium salt, present in excess amount, during the synthesis of vanillin or 4-hydroxy-3-methoxybenzaldehyde.

BACKGROUND OF THE INVENTION

Hydroxyaromatic and alkoxyaromatic aldehydes are very important products, which are used as flavors and fragrances and as intermediates in numerous fields, such as, for example, agrochemicals, pharmacy, cosmetology, and other industries.

The ortho- and para-hydroxybenzaldehydes, 4-hydroxy-3-methoxybenzaldehyde and 3-ethoxy-4-hydroxybenzaldehyde, named "vanillin" and "ethylvanillin" respectively, are among the most important products.

Various processes have been proposed for the synthesis of aromatic aldehydes.

The most important processes are based on the functionalization of a phenolic starting compound, phenol, catechol derivative, guaiacol (or 2-methoxyphenol), guaethol (or 2-ethoxyphenol).

In this type of process, the phenolic compound is generally involved in a salified form, for example, in the form of a sodium salt.

Thus, for example, numerous processes for preparing vanillin involve a guaiacol salt as substrate, to which is then added a formyl group, in the position para to the hydroxyl group, by various methods.

One conventional route to vanillin involves a condensation reaction of glyoxylic acid with guaiacol, in basic medium, to give 4-hydroxy-3-methoxymandelic acid. This product is then oxidized to produce vanillin.

The reaction is commonly conducted in the presence of sodium hydroxide and with an excess of guaiacol, with glyoxylic acid being the deficit reactant.

Thus, at the end of the condensation reaction, an aqueous reaction mixture is obtained that comprises the sodium salt of 4-hydroxy-3-methoxymandelic acid, the precursor to vanillin, secondary products, such as the sodium salts of 2-hydroxy-3-methoxymandelic acid and 4-hydroxy-5-methoxy-1,3-dimandelic acid, and a greater or lesser excess of sodium guaiacolate.

In this reaction mixture, therefore, there are a number of types of salified phenolic compounds present, namely guaiacol in excess in the form of sodium guaiacolate, and the products of the reaction which are also salified phenolic compounds, such as the sodium salts of 4-hydroxy-3-methoxymandelic acid, 2-hydroxy-3-methoxymandelic acid, and 4-hydroxy-5-methoxy-1,3-dimandelic acid.

For economic reasons it is important to recover the unreacted starting substrate. However, the operation is not easy, since the guaiacol is in the form of sodium guaiacolate and is present alongside phenolic compounds which are also salified and have a closely related structure.

In certain processes described in the prior art, especially in FR 2 132 364, the sodium guaiacolate, at the end of the condensation reaction, is converted to guaiacol by an acid treatment, most often with sulfuric acid.

The unconverted guaiacol is then extracted from the acid solution by an extraction treatment using a hydrocarbon, for example, benzene or toluene.

The drawback of a method of this kind is that it employs an organic solvent, thereby giving rise to additional distillation operations in order to be able to recycle the organic solvent and the substrate recovered. Moreover, in the course of the distillation, there are secondary reactions which lead to the formation of heavy products.

Furthermore, the neutralization of sodium guaiacolate with sulfuric acid produces sodium sulfate, leading to the formation of substantial salt effluents.

Moreover, the guaiacol recovered must be salified again in order to be introduced into the condensation reaction with glyoxylic acid.

Similarly, the reaction mixture, comprising the mandelic compounds with a free hydroxyl group, must be salified again in order to be introduced into the oxidation reaction that allows vanillin to be obtained.

In order to overcome these drawbacks, the invention provides a method that allows the excess of phenolic starting compound in salified form, especially sodium guaiacolate, to be recovered, by a method which does not involve this step of neutralizing sodium guaiacolate to guaiacol, with the attendant need for said guaiacol to be extracted using an organic solvent which must subsequently be separated by distillation.

SUMMARY OF THE INVENTION

A method has now been found, and constitutes the subject of the present invention, of separating phenolic compounds in salified form from an aqueous reaction mixture resulting from the reaction of a phenolic compound and glyoxylic acid in the presence of a base, leading to a reaction mixture comprising at least the excess of phenolic starting compound in salified form and the various mandelic compounds in salified form, resulting from the reaction, characterized in that said reaction mixture comprising the phenolic starting compound in salified form is contacted with an adsorbent support, leading to the selective adsorption of said phenolic compound on said support, and to the recovery of an aqueous stream comprising the mandelic compounds in salified form obtained from the reaction, and in that the phenolic compound attached to the adsorbent is desorbed by a regenerative treatment of said adsorbent.

DETAILED DESCRIPTION

In the description below of the present invention, the term "phenolic starting compound" means a benzene compound in which at least one hydrogen atom directly bonded to the benzene nucleus is substituted by a hydroxyl group.

In accordance with the method of the invention, it has been found, in the case of the treatment of an aqueous, reaction mixture comprising sodium guaiacolate, that the latter can be adsorbed on the adsorbent substrate thereby allowing it to be separated and subsequently, after desorption, recycled to the synthesis step without the need to pass via a step of acidification of the sodium guaiacolate in order to convert it to guaiacol, which is recovered and then subjected to a further basic treatment, since the compound employed in the condensation step is a phenolate.

In order to illustrate the method of the invention, the Applicant is citing the case of the separation of sodium guaiacolate from the aqueous mixture from condensation of sodium guaiacolate and glyoxylic acid.

However, the method of the invention is not limited to the separation of this substrate, and is also suitable for phenolic starting compounds in salified form corresponding to the following formula:

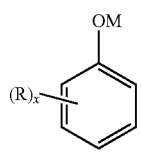

(I)

in which formula:
R is an alkyl or alkoxy group having from 1 to 4 carbon atoms, or a halogen atom,
x is a number from 0 to 3, and more preferably is 1, and
M represents a cation of a metallic element from group (IA) of the periodic table, namely lithium, sodium, potassium, rubidium, and cesium, or an ammonium cation.

In the formula (I), M is preferably sodium.

Examples of alkyl groups that may be mentioned include linear or branched alkyl groups having from 1 to 4 carbon atoms, such as methyl, ethyl, n-propyl, isopropyl, n-butyl, isobutyl, sec-butyl, and tert-butyl. Among these, the methyl and ethyl groups are preferred.

Examples of linear or branched alkoxy groups having from 1 to 4 carbon atoms include methoxy, ethoxy, n-propoxy, isopropoxy, n-butoxy, isobutoxy, and sec-butoxy groups. Methoxy and ethoxy groups are preferred.

R also represents a halogen atom, preferably fluorine, chlorine, and bromine, and more preferably fluorine.

With regard to the nature of R, it should be noted that the list of substituents given is not limitative, and other substituents may be envisaged insofar as they do not disrupt the separation of the compound of formula (I).

Illustrative instances of compounds corresponding to the formula (I) include, more particularly, the salts of compounds selected from the group consisting of the following: phenol, guaiacol, 3-methoxyphenol, guaethol, 3-ethoxyphenol, 2-isopropoxyphenol, 3-isopropoxyphenol, 2-methoxy-5-methylphenol, 2-methoxy-6-methylphenol, 2-methoxy-6-tert-butylphenol, 3-chloro-5-methoxyphenol, 2,3-dimethoxy-5-methylphenol, 2,3-dimethoxyphenol, 2,6-dimethoxyphenol, 3,5-dimethoxyphenol, cresols, tert-butylphenol, 2-methoxyphenol, and 4-methoxyphenol.

The preferred compounds of formula (I) are phenol, guaiacol, and guaethol.

According to the invention, the method of the invention is applied to the aqueous reaction mixture obtained from the reaction of a phenolic compound in salified form of formula (I) and glyoxylic acid.

The condensation reaction of the phenolic compound of formula (I) and glyoxylic acid may be conducted in the presence of an ammonium hydroxide, but more preferably in the presence of an alkali metal hydroxide, which may be sodium hydroxide or potassium hydroxide. For economic reasons it is preferred to select sodium hydroxide.

With regard to the glyoxylic acid, an aqueous solution of glyoxylic acid is employed that has a concentration of, for example, between 15% and 70% by weight.

The glyoxylic acid is reacted with the phenolic compound of formula (I) in excess. The molar ratio between the phenolic compound of formula (I) and the glyoxylic acid is between 1.1 and 4.0, preferably between 1.5 and 3.0.

The alkali metal hydroxide solution employed has a concentration of generally between 10% and 50% by weight.

The amount of alkali metal hydroxide introduced into the reaction mixture takes account of the amount needed in order to salify the hydroxyl function of the phenolic compound of formula (I), and the amount needed to salify the carboxyl function of the glyoxylic acid.

The concentration of the phenolic compound of formula (I) is preferably between 0.5 and 1.5 mol/liter.

The temperature of the reaction is selected advantageously between 20° C. and 60° C.

The reaction is conducted at atmospheric pressure but under a controlled atmosphere of inert gases, preferably nitrogen or rare gases, especially argon. It is preferred to select nitrogen.

After the phenolic compound of formula (I) has been contacted with the glyoxylic acid and the alkali metal hydroxide, the reaction mixture is maintained with stirring and at the temperature selected from the aforementioned range, for a variable duration of from 1 to 10 hours.

At the end of the reaction, an aqueous reaction mixture is obtained that comprises the excess of phenolic compound in salified form corresponding to the formula (I) and various mandelic compounds in salified form, denoted by the expression "mandelic compounds" and corresponding to the following formulae:

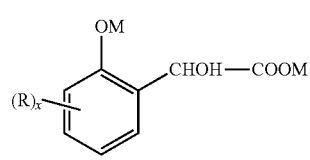

(IIa)

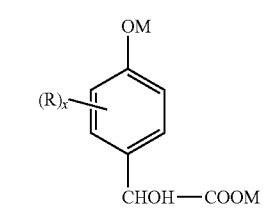

(IIb)

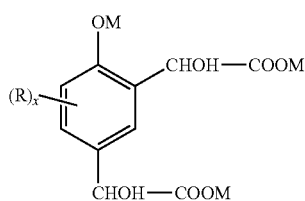

(IIc)

in which formulae M, R, and x are as defined for the formula (I).

The preferred mandelic compounds correspond to the formulae (IIa), (IIb), and (IIc), in which M represents a sodium atom, x is a number from 0 to 3, and preferably is 1, and the groups R, which are identical or different, represent an alkyl or alkoxy group having from 1 to 4 carbon atoms, preferably a methoxy or ethoxy group, or a halogen atom.

The invention is applied more particularly, in the context of the preparation of vanillin, to an aqueous mixture comprising sodium guaiacolate and mandelic compounds in salified form: 4-hydroxy-3-methoxymandelic acid, 2-hydroxy-3-methoxymandelic acid, 4-hydroxy-5-methoxy-1,3-dimandelic acid, in salified form.

The invention is also applied preferably, for the preparation of ethylvanillin, to a reaction mixture which is an aqueous mixture comprising sodium guaetholate and mandelic compounds in salified form: 3-ethoxy-4-hydroxymandelic acid, 3-ethoxy-2-hydroxymandelic acid, 5-ethoxy-4-hydroxy-1,3-dimandelic acid, in salified form.

The concentration by weight of the phenolic starting compound in salified form, preferably sodium guaiacolate or sodium guaetholate, varies generally between 1% and 20% by weight, preferably between 5% and 10% by weight.

The concentration by weight of mandelic compounds (o-, p-, and di-mandelate) in the reaction mixture is typically between 3% and 30% by weight, preferably between 5% and 20% by weight.

The method of the invention of separating the phenolic compound in salified form is therefore implemented on the aqueous reaction mixture as defined above.

In the case of the preparation of vanillin and of ethylvanillin, the mixture therefore comprises sodium guaiacolate or sodium guaetholate and various reaction products, namely monofunctional or difunctional sodium mandelates as specified in accordance with formulae (IIa), (IIb), and (IIc), predominantly the compound of formula (IIb).

In accordance with the method of the invention, the reaction mixture as described above is contacted with an adsorbent support, leading to the selective adsorption on the support of the phenolic compound, and to the recovery of an aqueous stream comprising the various mandelic compounds, and then the phenolic compound is desorbed by regeneration of the adsorbent support by an appropriate means, preferably using a base.

An adsorbent support is a solid support capable of adsorbing on its surface the molecules of a substrate referred to as the "adsorbate" by Van Der Waals bonding.

Throughout the rest of the text, the adsorbent support will be referred to more simply as "adsorbent".

The adsorbents are generally supports which have a very high specific surface area and exhibit an internal porosity.

The specific surface areas indicated refer to a specific surface area determined by the method of BRUNEAU-EMMETT-TELLER as described in "The Journal of American Society 60, 309 (1938)".

The adsorbent must be selected with an eye to a number of requirements.

The adsorbent must be physically and chemically stable toward the operating conditions.

The adsorbent must have a high capacity to adsorb the adsorbate.

The efficiency of the adsorption is measured as a percentage of the adsorbate relative to the mass of the adsorbent. It is situated generally between 10% and 50% by weight.

The adsorbent must have a high selectivity of adsorption for the phenolic compound relative to the mandelic compounds.

The adsorbent must be easy to regenerate, which means that the adsorbate must be easily desorbed from the adsorbent support.

Adsorbents which can be used in the method of the invention include, in particular, activated carbons, adsorbent polymers, zeolites, and molecular sieves.

The adsorbent used according to the present invention may be an activated carbon.

Numerous grades of active carbons exist, and the carbons which may be used include "physical" carbons, which result from a step of high-temperature calcining of a carbon-containing raw material, generally followed by a step of thermal activation for enhancing the adsorbency of said material.

The active carbon may be based on coal, peat, lignite or petroleum distillation residues, or on the basis of any carbon-rich organic vegetable material: wood, barks, twigs, wood pulp, fruit shells, especially coconut shells and groundnut shells.

The post-calcining treatments are aimed at eliminating the products (minerals, tars) which obstruct the pores.

The post-combustion treatments may be physical activation, which involves a further combustion at high temperature, carried out in a stream of air and steam, which are injected under pressure, which will produce a narrow porosity on the surface of the carbon, substantially enhancing its surface area and its adsorbency.

Activation may also be carried out chemically, as for example using nitric acid or phosphoric acid, leading to an active carbon having relatively large pores.

The diameter of the pores is also dependent on the pores which exist in the raw material used. Very dense wood and coconut shells give micropores (<2 nm), while medium white woods give mesopores (between 2 and 50 nm) or macropores (>50 nm).

The surface area developed by the active carbon is immense: one gram of active carbon has a specific surface area of between 400 and 2500 $m^2/g$, preferably between 500 and 1000 $m^2/g$.

The iodine index, which defines the number of mg of iodine adsorbed per g of active carbon (ASTM D4607-94), is usually greater than or equal to 1000 and is generally between 1000 and 1300.

The active carbons may be employed in the form of granules, especially extrudates, having a size ranging, for example, from 0.4 to 2 mm, preferably from 0.5 to 1.5 mm (ASTM D2862-97).

The invention does not rule out the use of carbon-containing adsorbents formed, for example, by pyrolysis of polymeric resins.

Adsorbents suitable for the invention are obtained by pyrolysis of macrocrosslinked sulfonated styrene/divinylbenzene ion-exchange resin.

Reference may be made in particular to U.S. Pat. No. 5,094,754. Such adsorbents are sold by Rohm and Haas Company, under the registered trade mark Ambersorb, as for example Ambersorb 563.

Another type of adsorbents suitable for the method of the invention are the adsorbent polymers.

Adsorbent polymers generally take the form of beads having a porous structure.

The base polymers are polystyrenes, more particularly styrene-divinylbenzene copolymers, or are polyacrylics, especially divinylbenzene-acrylic ester copolymers, or are phenolic polymers, more particularly phenol/formaldehyde copolymers.

The porosity is created by a high degree of crosslinking of the polymer.

Polymeric adsorbents generally have a specific surface area of from 100 to 1000 $m^2/g$, preferably between 400 and 800 $m^2/g$.

They are generally mesoporous materials having a pore size of from 4 to 60 nm: their internal porosity is between 0.4 and 1.2 $cm^3/g$.

Preferred adsorbents are inert adsorbents containing no functional groups, and more particularly mesoporous copolymers of styrene and divinylbenzene with a high degree of crosslinking and a high porosity.

Suitable more particularly for the implementation of the method of the invention are the mesoporous adsorbent polymers of styrene and divinylbenzene that are sold by Rohm and Haas under the trade name Amberlite XAD, and more preferably the following polymers: Amberlite XAD FPX66; Amberlite XAD 4; Amberlite XAD 16; Amberlite XAD 761; Amberlite XAD 1180N; Amberlite XAD 1600N; Amberlite XAD 18; Amberlite XAD7 HP.

Other adsorbent polymers that may be mentioned include those sold under the name Purolite Hypersol Macronet, Purolite Purosorb; and also those sold by Lanxess, and more particularly Lewatit VP OC 1064 MD PH and Lewatit VP OC 1163.

As other adsorbents, mention may also be made of zeolites.

A zeolite is a crystalline tectosilicate of natural or synthetic origin, in which the crystals result from the three-dimensional assembly of tetrahedral units of $SiO_4$ and $TO_4$, where T represents a trivalent element such as aluminum, gallium, boron, and iron, preferably aluminum.

Aluminosilicate zeolites are the most common.

Within the crystalline network, zeolites have a system of cavities which are connected to one another by channels having a well-defined diameter, referred to as the pores, with the channels forming a one-dimensional, two-dimensional or three-dimensional network.

In the method of the invention, it is preferred to employ zeolites having a two-dimensional or three-dimensional network.

Although it is possible to employ a natural zeolite, preference is given to selecting a synthetic zeolite, which has constant physicochemical characteristics.

It is advantageous to select a zeolite having an average pore diameter of greater than or equal to 6, and preferably of between 6 and 8 Å.

Examples of zeolites particularly suitable for implementing the method of the invention include zeolites with a two-dimensional network, more particularly mordenite zeolites; zeolites having a three-dimensional network, more particularly β zeolites, and faujasite zeolites, more particularly Y zeolites; or mesoporous MCM zeolites.

As an indication, it will be specified that the average pore diameter of the mordenite, β and Y zeolites is of the order, respectively, of 6.5 Å, 6.8 Å, and 7.2 Å.

In the various zeolites, the Si/Al ratio may vary widely.

Mordenites have a molar Si/Al ratio of 5 to 50.

β Zeolites have a molar Si/Al ratio of more than 8, preferably of between 10 and 100, and more preferably of between 12 and 50.

The Y zeolites, especially the zeolites obtained after dealumination treatment (for example hydrotreatment, washing using hydrochloric acid or treatment by $SiCl_4$), have molar Si/Al ratios of more than 3, preferably of between 6 and 100.

Mesoporous MCM zeolites, more particularly MCM-41 and MCM-48, have molar Si/Al ratios of between 10 and 100, preferably of between 15 and 40. They have a BET specific surface area of between 700 and 1000 $m^2/g$ and a pore diameter ranging generally between 15 and 40 Å.

Among all of these zeolites, it is preferred in the method of the invention to employ β and Y zeolites.

The zeolites employed in the method of the invention are known products which are described in the literature [cf. Atlas of zeolite structure types by W. M. Meier and D. H. Olson published by the Structure Commission of the International Zeolite Association (1978)].

It is possible to employ commercially available zeolites or else to synthesize them by the methods described in the literature, particularly according to the references referred to in the aforementioned Atlas.

Also suitable for the method of the invention are molecular sieves.

Molecular sieves are synthetic zeolites which are characterized by a crystalline structure and a regular pore diameter.

They are metallic aluminosilicates which possess a three-dimensional crystalline structure composed of an assembly of $SiO_4$ and $AlO_4$ tetrahedra, and containing cations such as $Na^+$, $K^+$ or $Ca^{++}$, to make the system electrically neutral.

The tetrahedra are assembled in such a way that they constitute a truncated octahedron. These octahedra are themselves arranged according to a simple cubic crystalline structure, forming a network with cavities having an approximate diameter of 11.5 Å, these cavities being accessible via openings or pores.

The family of molecular sieves that is referred to commonly as MS includes the 3A, 4A and 5A molecular sieves.

Molecular sieves of type A are characterized by a molar Si/Al ratio of close to 1.

The opening size of pores varies depending on the type of molecular sieve, since the pores may be blocked by cations and by cation exchange, and so it becomes possible to modify the size of the pores.

When these cations are derived from sodium, the pores have an opening diameter of 4.1 Å, and the molecular sieve is then referred to as a 4A sieve.

Molecular sieve 4A is obtained by replacing a large part of the sodium ions with potassium ions, the diameter of the pores being approximately 3 Å.

Molecular sieve 5A is produced by replacing the sodium ions with calcium ions, the diameter of the pores in that case being of the order of 5 Å.

3A, 4A or 5A sieves are available commercially, in powder form and optionally in the form of compositions with other substances, especially a clay-based binder which may take the form of granules, beads or extrudates.

Among the various aforementioned sieves, sieve 5A is capable of intervening preferentially in the method of the invention.

In accordance with the method of the invention, the reaction mixture obtained at the end of the condensation reaction is passed onto the adsorbent support.

The stream is therefore at a temperature close to the condensation temperature of between 20° C. and 60° C.

Generally speaking, the adsorbent support is placed in a stirred reactor or else in a column, with the mixture being introduced generally from top to bottom.

The amount of adsorbent support employed is determined on the basis of the adsorption efficiency of the adsorbent support.

As mentioned above, the adsorption efficiency varies generally between 10% and 50%. Accordingly, in order to have complete adsorption, the amount of adsorbent employed is adapted: the lower the adsorption efficiency, the higher the amount of adsorbent employed.

It will be specified that the amount of adsorbent represents at least from 2 to 10 times the weight of the phenolic compound in salified form that is to be adsorbed. It is preferred to employ an excess of adsorbent, for example an excess of 10% to 20% of the weight of adsorbent calculated.

At the column bottom an aqueous stream is recovered that comprises all of the mandelic compounds in salified form, while the phenolic compound is adsorbed on the support.

The aqueous stream comprising the mandelic compounds in salified form may be directly input into the oxidizing operation, thereby making it possible to obtain the aromatic aldehyde corresponding to the mandelic compounds in salified form.

In a subsequent step, the phenolic compound in salified form is recovered by regeneration of the adsorbent.

Regeneration of the adsorbent by means of a base is selected with preference.

Suitable bases include, in particular, sodium hydroxide or potassium hydroxide.

For this purpose, a basic treatment is carried out, preferably using a basic aqueous solution, having a concentration of 1% to 10% by weight, and more preferably between 2% and 8% by weight. Sodium hydroxide is typically used.

The amount of base employed is at least equal to the amount of phenolic compound in salified form that is to be regenerated.

A solution is thus obtained of the phenolic compound, which is salified and can therefore be recycled directly to the condensation step.

As mentioned above, the method of the invention makes it possible to separate an aqueous stream comprising the various mandelic compounds in salified form.

Accordingly, the method of the invention allows access to hydroxyaromatic aldehydes corresponding to the formulae (IIa), (IIb), and (IIc) in which the glycol group of formula —CHOH—COOH is replaced by a formyl group CHO.

The oxidation reaction may be conducted according to the techniques that are described in the literature. Thus it is possible to use the catalysts that are conventionally used in oxidation reactions of mandelic compounds in a basic medium.

The oxidation is generally conducted by oxygen or air under pressure, in the presence of an appropriate catalyst such as, for example, derivatives of chromium, manganese, iron, cobalt, nickel, copper, zinc, bismuth, aluminum, silver, vanadium or osmium.

It should be noted that this list is not limitative.

It is possible, very particularly, to employ oxides, sulfates, halides, and acetates of said metallic elements.

It is also possible to use a catalyst comprising at least two metallic elements. Reference may be made more particularly to WO 2008/148760, which proposes the use of a catalyst system comprising at least two metallic elements, $M_1$ and $M_2$, which are selected from the group consisting of copper, nickel, cobalt, iron, and manganese.

Accordingly, the invention allows easy access to hydroxybenzaldehydes, and more particularly to vanillin and its analogs, for example, 3-ethylvanillin and 3-isopropylvanillin, by oxidation, respectively, of p-hydroxymandelic acid and of 4-hydroxy-3-methoxymandelic acid, 3-ethoxy-4-hydroxymandelic acid, or 4-hydroxy-3-isopropoxymandelic acid.

Working examples of the invention are given below by way of illustration and without any limitative character.

In the examples, the selectivity of the reaction is defined as the following molar ratio: [guaiacol]adsorbed/([guaiacol]adsorbed+[mandelate] adsorbed).

EXAMPLES

Example 1

In this example, the adsorbent used is 5A molecular sieve.

This solid is a calcium aluminosilicate. It possesses a pore diameter of 0.5 nm.

A Schott tube is charged with 20 g of a stream comprising 0.95 g of sodium guaiacolate (0.0065 mol) and 1.32 g of sodium p-mandelate (0.0055 mol) of formula:

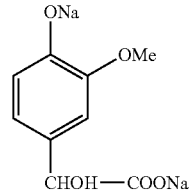

Then 2 g of 5A molecular sieve are added, and the reaction mixture is stirred at 40° C. throughout the duration of the adsorption.

The adsorption is monitored by high-performance liquid chromatography analysis of said solution.

After 15 minutes, 45% of guaiacolate is adsorbed.

After 1 hour 30 minutes, 55% by weight of guaiacolate is adsorbed (expressed relative to the total weight of guaiacolate present in the solution to be treated), with no attachment of mandelates.

The ratio defining the selectivity is 1.

Example 2

In this example, a Y zeolite is employed, namely the hydrophobic zeolite Wessalith DAY 55. The pore diameter of this zeolite is 0.72 nm.

Example 1 is repeated, with the only difference that the nature of the adsorbent is changed.

With this adsorbent, 44% of guaiacolate is adsorbed after 15 minutes, with no adsorption of mandelates.

The selectivity obtained is 1.

Example 3

In this example, an adsorbent polymer is employed which is called Amberlite XAD16, which is a copolymer of styrene and divinylbenzene and is a nonionic polymer. It is present in the form of beads, it possesses a large specific surface area of more than 700 m$^2$/g, and its structure is very porous: the average pore size is 10 nm.

Example 1 is repeated, with the only difference that the nature of the adsorbent is changed.

With this adsorbent, the selectivity obtained is 1, and a 60% solution of guaiacolate remains.

Example 4

In this example, active carbons in the form of granules or extrudates are employed as adsorbents.

The active carbons used have a high specific surface area (>1100 m$^2$/g) and originate from the companies Norit, Ceca, and Eurocarb.

Example 1 is repeated, with the only difference that the nature of the adsorbent is changed.

The results obtained after 30 minutes are indicated in table (I).

TABLE (I)

| Active carbon used | Origin | Specific surface area | Selectivity | % of guaiacolate adsorbed in relation to total weight of guaiacolate |
|---|---|---|---|---|
| Norit ROX 8 | Coal | 1225 | 1 | 70 |
| Acticarbone BGX260 | Pine | 1700 | 1 | 76 |
| Chemviron CAL | Coconut | 1300 | 1 | 81 |

Example 5

In this example, the active carbon Eurocarb HT5 is employed, which is based on coconut. It is present in the form of grains and possesses a specific surface area of 1400 m$^2$/g.

The carbon is employed in a 300 ml column with a diameter of 2.8 cm and a height of 24 cm.

The volume of carbon is 150 ml.

The column is maintained under atmospheric pressure at 35° C.

This carbon is percolated at a rate of 1.5 m/h with a stream comprising 4.4% of sodium guaiacolate and 6.6% of mandelic compounds in sodium salt form (o-, p-, and di-mandelate), obtained from a condensation reaction between glyoxylic acid and guaiacol, in the presence of sodium hydroxide, conducted according to the teaching of the prior art (WO 99/65853), and corresponding to the formulae (IIa), (IIb), and (IIc) in which R represents a methoxy group, x is 1, and M is sodium.

In this example, 540 g of the stream as defined above are percolated through the carbon.

At the outlet from the column, 340 g of a stream which is free from sodium guaiacolate and contains all of the mandelic compounds in sodium salt form that were charged is recovered.

The ratio which defines the selectivity is 1.

The sodium guaiacolate adsorbed on the carbon is recovered by treatment with sodium hydroxide.

A 2% by weight aqueous solution of sodium hydroxide is percolated through the carbon at a rate of 2 m/s.

A stream is recovered which contains sodium guaiacolate with a yield of 60% by weight, the yield being defined as the weight ratio (in %) between the guaiacolate recovered and the guaiacolate introduced.

This guaiacolate may be directly recycled to the condensation step.

The stream at the column outlet that contains the mandelic compounds in salified form is then oxidized without further addition of aqueous sodium hydroxide solution.

The stream is charged to a 316 L stainless-steel reactor equipped with mechanical stirring, baffles, and an air inlet.

This reaction mixture is admixed with a catalyst system comprising $CoCl_2.6H_2O$ and $CuSO_4.5H_2O$, which are employed, respectively, in an amount, expressed as molar percentage of mandelic compounds, of 0.125 and 0.125.

The mixture is subsequently heated to 80° C. and air is introduced at a rate of 1.6 L/h.

After 30 minutes of reaction, a selectivity of the reaction for vanillin (expressed by the ratio between the number of moles of vanillin formed and the number of moles of p-mandelate converted) of 98% is obtained.

Example 6

Example 1 is reproduced, with the sole difference that the reaction mixture introduced results from the reaction of guaethol and glyoxylic acid in the presence of sodium hydroxide, and therefore comprises sodium guaetholate and the mandelic compounds in sodium salt form (o-, p-, and di-mandelate) which correspond to the formulae (IIa), (IIb), and (IIc) in which R represents an ethoxy group, x is 1, and M is sodium.

The adsorbent used in this example is the active carbon Eurocarb HT5.

After stirring for 1 hour and 30 minutes, a mixture is obtained which contains the entirety of the mandelic compounds, in the form of sodium salts, and 31% of sodium guaetholate.

With this adsorbent support, the ratio which defines the selectivity is 1.

The invention claimed is:

1. A method of separating phenolic compounds, the method comprising separating the phenolic compounds in salified form from an aqueous reaction mixture resulting from a reaction of a phenolic compound and glyoxylic acid in the presence of a base, leading to a reaction mixture comprising at least an excess of phenolic starting compound in salified form and various mandelic compounds in salified form, resulting from the reaction, wherein the reaction mixture comprising the phenolic starting compound in salified form is contacted with an inert adsorbent support comprising no functional groups, leading to selective adsorption of said phenolic compound on said support, and to recovery of an aqueous stream comprising the mandelic compounds in salified form obtained from the reaction, and in that the phenolic compound fixed on the adsorbent is desorbed by a regenerative treatment of said adsorbent.

2. The method as defined by claim 1, wherein the reaction mixture comprises a phenolic compound in salified form corresponding to the following formula:

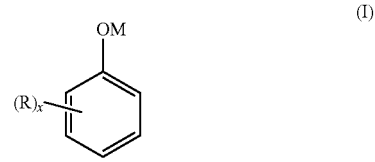

(I)

in which formula:
R is an alkyl or alkoxy group having from 1 to 4 carbon atoms, or a halogen atom,
x is a number from 0 to 3, and M is a cation of a metallic element from group (IA) of the periodic table.

3. The method as defined by claim 1, wherein the phenolic compound in salified form of formula (I) is sodium guaiacolate or sodium guaetholate.

4. The method as defined by claim 1, wherein the reaction mixture comprises the phenolic compound in salified form at a concentration of from 1% to 20% by weight.

5. The method as defined by claim 1, wherein the reaction mixture comprises reaction products which are mandelic acids in salified form at a concentration of from 3% to 30% by weight.

6. The method as defined by claim 1, wherein the reaction mixture is an aqueous mixture comprising sodium guaiacolate and mandelic compounds: 4-hydroxy-3-methoxymandelic acid, 2-hydroxy-3-methoxymandelic acid, 4-hydroxy-5-methoxy-1,3-dimandelic acid.

7. The method as defined by claim 1, wherein the inert adsorbent containing no functional groups is selected from the group consisting of activated carbons, inert adsorbent polymers containing no functional groups, zeolites, and molecular sieves.

8. The method as defined by claim 7, wherein the adsorbent is an activated carbon based on coal, peat, lignite, or petroleum distillation residues, or on the basis of any carbon-rich organic vegetable matter from the group consisting of wood, barks, twigs, wood pulp, shells of fruits.

9. The method as defined by claim 7, wherein the adsorbent is a carbon-containing adsorbent resulting from the pyrolysis of a polymeric resin.

10. The method as defined by claim 7, wherein the adsorbent is an inert adsorbent polymer containing no functional groups having a porous structure.

11. The method as defined by claim 7, wherein the adsorbent is a polystyrene polymer, a polyacrylic polymer, or a phenolic polymer.

12. The method as defined by claim 7, wherein the inert adsorbent polymer containing no functional groups is selected from the group consisting of mesoporous adsorbent polymer of styrene and divinylbenzene called Amberlite XAD, an adsorbent polymer called Purolite Hypersol Macronet, Purolite Purosorb; and a polymer called Lewatit VP OC 1064 MD PH and Lewatit VP OC 1163.

13. The method as defined by claim 7, wherein the adsorbent is a zeolite having an average pore diameter of greater than or equal to 6 Å.

14. The method as defined by claim 7, wherein the adsorbent is a mordenite zeolite; a β zeolite, a faujasite zeolite, a Y zeolite; or a mesoporous MCM zeolite.

15. The method as defined by claim 7, wherein the adsorbent is a molecular sieve.

16. The method as defined by claim 1, wherein the amount of adsorbent support employed represents at least from 2 to 10 times the weight of the phenolic compound in salified form that is to be adsorbed.

17. The method as defined by claim 1, wherein the phenolic compound in salified form is recovered by regeneration of the adsorbent by a basic treatment, preferably by means of an aqueous sodium hydroxide solution.

18. The method as defined by claim 2, wherein the cation of the metallic element from group (IA) if the periodic table is selected from the group consisting of lithium, sodium, potassium, rubidium, cesium or an ammonium cation.

19. The method as defined by claim 11, wherein the polystyrene polymer is a styrene-divinylbenzene copolymer.

20. The method as defined by claim 11, wherein the polyacrylic polymer is a divinylbenzene-acrylic ester copolymer.

21. The method as defined by claim 11, wherein the phenolic polymer is a phenol formaldehyde copolymer.

22. The method as defined by claim 15, wherein the molecular sieve is a 5 Å molecular sieve.

23. The method as defined by claim 17, wherein the phenolic compound is recovered by means of an aqueous sodium solution.

* * * * *